US010012624B2

(12) United States Patent
Witt et al.

(10) Patent No.: US 10,012,624 B2
(45) Date of Patent: *Jul. 3, 2018

(54) METHOD TRANSFER BETWEEN FLUIDIC DEVICES CONSIDERING DEVIATIONS FROM IDEAL BEHAVIOR

(71) Applicant: Agilent Technologies, Inc., Santa Clara, CA (US)

(72) Inventors: Klaus Witt, Waldbronn (DE); Herbert Anderer; Alwin Ritzmann, Waldbronn (DE); Dominik Ruf, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 175 days.

This patent is subject to a terminal disclaimer.

(21) Appl. No.: 15/215,233

(22) Filed: Jul. 20, 2016

(65) Prior Publication Data

US 2016/0327528 A1     Nov. 10, 2016

Related U.S. Application Data

(63) Continuation of application No. 13/062,838, filed as application No. PCT/EP2008/061858 on Sep. 8, 2008, now Pat. No. 9,423,384.

(51) Int. Cl.
*G01N 30/02* (2006.01)
*G01N 30/00* (2006.01)
(Continued)

(52) U.S. Cl.
CPC .............. *G01N 30/86* (2013.01); *F17D 3/00* (2013.01); *G01N 30/02* (2013.01); *G01N 30/34* (2013.01);
(Continued)

(58) Field of Classification Search
None
See application file for complete search history.

(56) References Cited

U.S. PATENT DOCUMENTS

| 2002/0010566 A1 | 1/2002 | Chester et al. |
| 2008/0142444 A1 | 6/2008 | Toyosaki |

(Continued)

FOREIGN PATENT DOCUMENTS

| JP | 07-012799 A | 1/1995 |
| JP | 2001281230 A | 10/2001 |
| JP | 2009281897 A | 12/2009 |

OTHER PUBLICATIONS

Garcia-Lavandeira et al: "Computer-assisted transfer of programmed elutions in a reversed-phase high-performance liquid chromatography" Journal of Chromatography, Elsevier Science Publishers BY Amsterdam, NL, vol. 1128, No. 1-2, Sep. 22, 2006, pp. 17-26. (Year: 2006).*

(Continued)

*Primary Examiner* — Jennifer Wecker

(57) ABSTRACT

An apparatus for deriving an operation mode from a first fluidic device to a second fluidic device, wherein the first fluidic device has a first target operation mode representing a desired behavior of the first fluidic device and has a first real operation mode representing the actual behavior of the first fluidic device, wherein the second fluidic device has a second target operation mode representing a desired behavior of the second fluidic device and has a second real operation mode representing the actual behavior of the second fluidic device, the apparatus comprising a first determining unit configured for determining the first real operation mode based on the first target operation mode and based on a preknown parameterization of the first fluidic device, and a second determining unit configured for determining the second target operation mode based on the determined (Continued)

first real operation mode and based on a preknown parameterization of the second fluidic device.

26 Claims, 8 Drawing Sheets

(51) Int. Cl.
    *F17D 3/00*     (2006.01)
    *G01N 30/86*     (2006.01)
    *G01N 30/34*     (2006.01)
    *G01N 33/48*     (2006.01)
    *H01J 49/44*     (2006.01)

(52) U.S. Cl.
    CPC ..... *G01N 30/8658* (2013.01); *G01N 30/8662* (2013.01); *G01N 30/8693* (2013.01); *Y10T 137/0318* (2015.04); *Y10T 137/8376* (2015.04)

(56) References Cited

U.S. PATENT DOCUMENTS

| | | |
|---|---|---|
| 2009/0126466 A1 | 5/2009 | Gilar et al. |
| 2009/0288473 A1 | 11/2009 | Suzuki et al. |
| 2016/0216239 A1 | 7/2016 | Aota et al. |

OTHER PUBLICATIONS

Garcia-Lavandeira et al: "Computer-assisted transfer of programmed elutions in a reversed-phase high-performance liquid chromatography" Journal of Chromatography, Elsevier Science Publishers B.V. Amsterdam, NL, vol. 1128, No. 1-2, Sep. 22, 2006, pp. 17-26, XP005629090, ISSN: 0021-9673.

Cela R; Lores M: "Preopt-W: A simulation program for off-line optimization of binary gradient separations in HPLC Fundamentals and Overview" Computers and Chesmistry, vol. 20, No. 2, Jun. 1996, pp. 175-191, XP002524315, Elsevier Science Ltd.

Garcia-Lavandeira J. et al: "Computer-assisted method development in liquid chromatography-mass spectrometry: New proposals" Journal of Chromatography, Elsevier Science Publishers B.V. Amsterdam, NL, vol. 1208, No. 1-2, Oct. 24, 2008, pp. 116-125, XP025504540, ISSN: 0021-9673.

Hendriks G. et al: "New practical algorithm for modelling retention times in gradient reversed-phase high-performance liquid chromatography" Journal of Chromatography, Elsevier Science Publishers B.V. Amsterdam, NL, vol. 1089, No. 1-2, Sep. 30, 2005, pp. 193-202, XP004996631, issn: 0021-9673.

Lourici L; Souici M. L.; Rebbani N; Messadi D.: "Independent of local properties mathematical models for the calculation of retention indices in programmed temperature gas chromatography." Analusis, No. 27, 1999, pp. 249-254, XP002524316.

International Search Report dated Apr. 20, 2009 for related International Application No. PCT/EP2008/061858.

John W. Dolan, "Dwell Volume Revisited", LCGC North America, vol. 24, No. 5, May 2006, pp. 458-466.

Non-final Office action dated May 5, 2014 from related U.S. Appl. No. 13/062,838.

Final Office action dated Sep. 17, 2014 from related U.S. Appl. No. 13/062,838.

Non-final Office action dated Jun. 5, 2015 from related U.S. Appl. No. 13/062,838.

Final Office action dated Nov. 27, 2015 from related U.S. Appl. No. 13/062,838.

International Search Report and Written Opinion dated Feb. 18, 2014, cited in US Pat. App. No. 2016/0216239.

\* cited by examiner

METHOD TRANSFER BETWEEN FLUIDIC DEVICES CONSIDERING DEVIATIONS FROM IDEAL BEHAVIOR

RELATED APPLICATIONS

This application is a continuation of U.S. patent application Ser. No. 13/062,838, now U.S. Pat. No. 9,423,384, filed May 4, 2011, titled METHOD TRANSFER BETWEEN FLUIDIC DEVICES CONSIDERING DEVIATIONS FROM IDEAL BEHAVIOR, which is the National Stage of International Application No. PCT/EP2008/061858, filed on 8 Sep. 2008 which designated the United States of America, and which international application was published as Publication No. WO 2010/025777; the contents of each of which are incorporated herein in their entireties.

BACKGROUND ART

The present invention relates to the operation of fluidic devices.

Fluidic devices are applied to execute various measurement tasks in order to measure any kind of physical parameter. Each fluidic device may have a specific driver with device specific commands. A programming software allows a user to design an operation mode of the fluidic device. As a result of such a design, the fluidic device may be operated in accordance with the designed operation mode.

More particularly, in liquid chromatography, a fluidic analyte may be pumped through a column comprising a material which is capable of separating different components of the fluidic analyte. Such a material, so-called beads, may be filled into a column tube which may be connected to other elements (like a control unit, containers including sample and/or buffers). Upstream of a column, the fluidic analyte is loaded into the liquid chromatography apparatus. A controller controls an amount of fluid to be pumped through the liquid chromatography apparatus, including controlling a composition and time-dependency of a solvent interacting with the fluidic analyte. Such a solvent may be a mixture of different constituents. The supply of these constituents for subsequent mixing is an example of an operation to be designed by an operator of a liquid chromatography device.

John W. Dolan, "Dwell Volume Revisited", LCGC North America. Volume 24, No. 5, May 2006, pages 458 to 466 discloses that the practical impact of a system dwell volume on retention and resolution in liquid chromatography is not something to take lightly. It is unfortunate that many chromatographers ignore dwell volume considerations when developing and transferring gradient LC methods. But even when, then it can be a tedious task, stuffed with pitfalls and limitations.

Hence, a conventional operation mode adjustment system for a fluidic device may be cumbersome.

DISCLOSURE

It is an object of the invention to provide a reliable and simple operation mode adjustment system for a fluidic device.

According to an exemplary embodiment, an apparatus (such as a computer or a workstation) for deriving (particularly for converting) an operation mode from a first fluidic device configuration (such as a first setup of a liquid chromatography apparatus) to a second fluidic device configuration (such as a second setup of a liquid chromatography apparatus) is provided, wherein the first fluidic device has a first target operation mode representing a desired behavior of the first fluidic device and has a first real operation mode representing the actual behavior of the first fluidic device, wherein the second fluidic device has a second target operation mode representing a desired behavior of the second fluidic device and has a second real operation mode representing the actual behavior of the second fluidic device, the apparatus comprising a first determining unit (such as a processor) adapted for determining the first real operation mode based on the first target operation mode and based on a preknown parameterization of the first fluidic device configuration, and a second determining unit (such as a processor) adapted for determining the second target operation mode based on the determined first real operation mode and based on a preknown parameterization of the second fluidic device configuration.

According to another exemplary embodiment, a method of deriving an operation mode from a first fluidic device or device configuration to a second fluidic device or a second fluidic device configuration is provided, wherein the first fluidic device has a first target operation mode representing a desired behavior of the first fluidic device and has a first real operation mode representing the actual behavior of the first fluidic device or configuration, wherein the second fluidic device has a second target operation mode representing a desired behavior of the second fluidic device and has a second real operation mode representing the actual behavior of the second fluidic device or configuration, the method comprising determining the first real operation mode based on the first target operation mode and based on a preknown parameterization of the first fluidic device, and determining the second target operation mode based on the determined first real operation mode and based on a preknown parameterization of the second fluidic device.

According to still another exemplary embodiment of the present invention, a software program or product is provided, preferably stored on a data carrier, for controlling or executing the method having the above mentioned features, when run on a data processing system such as a computer.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of measurement management. The measurement management scheme according to an embodiment of the invention can be performed or assisted by a computer program, i.e. by software, or by using one or more special electronic optimization circuits, i.e. in hardware, or in hybrid form, i.e. by means of software components and hardware components.

The term "operation mode" may particularly denote a workflow, an algorithm or a set of operation parameters defining as to how a fluidic device is to be operated or run. Thus, the operation mode may include a complete set of data which, when provided to the fluidic device, defines a dedicated operation of this fluidic device. For example, the operation mode may define a procedure of separating different components of fluids by the fluidic device (for example a recipe as to how to run a liquid chromatography, gas chromatography or gel electrophoresis experiment), a procedure of analyzing a medication (for example in a coupled liquid chromatography and mass spectroscopy device in which a metabolism of a drug in a human body may be investigated), a diagnostic procedure (for example for diagnosing a specific physiological condition based on an analysis of a sample), a procedure requiring official approval (for instance an approval procedure before the FDA, Food and Drug Administration, in the United States), a procedure of flushing the device (for example an algorithm according to which a rinse solution is supplied for removing traces of fluids from a previous investigation, thereby suppressing undesired crosstalk or contamination), a selection of a solvent for the fluidic device (for instance selecting multiple constituents of such a solvent, their relative concentrations, etc.), a procedure of applying a concentration gradient to the fluidic device (for example to perform a liquid chromatography analysis using a chromatographic column) and/or a selection of an operation temperature (and/or other physical parameters such as pressure) for the fluidic device. The operation mode may define a sequence of instructions providable to the fluidic device for operating the fluidic device. Such a set of instructions may be sufficient for running the fluidic device in accordance with a desired scheme.

The term "target operation mode" may particularly denote an operation mode which a user intends to obtain, i.e. an ideal operation mode. In contrast to this, a "real operation mode" may denote an operation mode obtained actually in practice when running a fluidic device in its actual configuration, so that a real operation mode may deviate from the ideal operation mode as a result of real world effects or parasitic effects occurring with the fluidic device or configuration when being operated. Such effects may relate to non-zero dead volumes, shape and mixing behavior of fluidic conduits, temperature and velocity profile generation due to friction between a fluid and a wall of a surrounding conduit, etc. For a precise operation of the device, the difference between target operation mode and real operation mode can be taken into account according to exemplary embodiments. For instance, effects resulting from a dwell volume of a liquid chromatography device may result in a difference between a target operation mode and a real operation mode.

The term "preknown parameterization" of the fluidic device may particularly denote a set of technical parameters of the fluidic device known beforehand, for instance stored in a database. Such physical properties may involve a transport characteristic which may include parameters such as volumes, dimensions, values of physical parameters such as pressure or temperature, and/or physical effects such as a model of friction occurring in a fluidic conduit which friction effects may be modeled, for example, according to the Hagen Poiseuille law. More particularly, the parameterization may consider a size of a fluidic device (for instance a dimension of a fluidic channel), a volume of a fluid conduit (such as a dead volume) of the fluidic device, a pump performance (such as the pump power and/or pump capacity) of the fluidic device, a delay parameter (such as a delay time after switching on a fluidic device) of operating the fluidic device, a friction parameter (for instance characterizing friction between a wall of a fluidic conduit and a fluid flowing through the conduit) of operating the fluidic device, a flush performance (particularly properties related to rinsing or flushing the fluidic device before operating it or between two subsequent operations) of the fluidic device, and/or a cooperation of different components of the fluidic sample (for instance the properties of a gradient applied to a chromatographic column which, for example, may be connected to the destination). Thus, a parameterization of the fluidic device may be denoted as a set of parameter values representing or defining physical effects by a number of parameters or functions as a basis for a computer model. Additionally or alternatively, empirically extracted transfer functions may be used to describe the actual system behavior of the fluidic device in its actual configuration.

The term "fluidic device" may particularly denote any apparatus which involves the transport, analysis or processing of a fluid. A fluid may denote a liquid, a gas or a combination of a liquid and a gas, and may optionally also include solid particles, for instance forming a gel or an emulsion. Such a fluid may comprise a fluidic solvent and/or a fluidic sample under analysis. Examples for fluidic devices are chemical analysis devices, life science apparatuses or any other biochemical analysis system such as a separation device for separating different components of a sample, particularly a liquid chromatography device.

According to an exemplary embodiment, a method or operation mode may be transferred from one technical system to another technical system, more particularly from one fluidic device to another fluidic device, or from a fluidic device in its first configuration to its second configuration. For instance in a scenario in which a first fluidic device is already certified (for instance by an official authority such as the FDA), a transfer of the certified method to another apparatus to be certified may involve significantly less effort than designing a completely new method or modifying the method all manually. Thus, a method which has already turned out to be successful in the past can be transferred with reduced development effort and certification effort to another similar machine. Hence, an exemplary embodiment provides a system for transferring a method from an old machine generation to a new machine of modern generation, comprising calculating on the basis of a first target operation mode and a configuration of the old machine at first a real operation mode of the old machine. This first real operation mode may describe how the old machine behaves in practice when being operated according to the first target operation mode in a real physical environment or implementation. Then, a desired operation mode for the new machine can be estimated on the basis of the real operation mode of the old machine and the configuration of the new machine. Particularly for separation devices, this may ensure compatibility of operation of the new machine with the old machine and may allow to design a method for a new machine with reasonable effort. Particularly the latter procedure of deriving a target operation mode for the new machine based on the real operation mode of the old machine and the configuration of the new machine may be executed by performing numeric fitting algorithms, if desired in an iterative manner. Thus, a least squares fit or a best fit according to another criteria may be considered as new operation mode. Such a transfer of a certified method may be particularly advantageous for pharmaceutical industry, where a machine is provided for analyzing medication and/or for performing diagnostics. Thus, such embodiments, especially when validated, may be advantageous for approval purposes, quality control, and reproducibility.

Next, further exemplary embodiments of the apparatus will be explained. However, these embodiments also apply to the method, to the software program and to the software product.

The apparatus may be adapted for converting an operation mode from the first fluidic device to the second fluidic device. Thus, an operation mode such as the liquid chromatography method which has already been established for the first fluidic device may be transferred for the second fluidic device as well, this way may be adapted to the specific requirements of the second device. A method transfer may include considering a dwell volume of the first and the second fluidic device. The dwell volume may be denoted as the system volume from the point where the solvents are mixed until they reach the column inlet. This may result in an unintentional isocratic hold at the beginning of each gradient run. Differences in dwell volume between LC systems should be considered when gradient methods are to be transferred. Retention times may be shifted by the difference in dwell time (the time it takes to flush out the dwell volume) on two individual systems or configurations, and early peaks in the chromatogram often exhibit differences in peak spacing as well as retention.

The first and the second fluidic device may both have an identical first portion offering the same functionality and may have a second portion by which the first fluidic device offers another functionality than the second fluidic device. A challenge during the method transfer is then the adaptation of the second part, whereas method portions related to the first part need not to be changed for the method conversion.

The operation mode may define a procedure of treating fluids by the respective fluidic device. Thus, the operation modes may include a set of instructions for operating the fluidic device so that a solvent and/or fluidic sample may be treated in a specific manner.

The target operation mode may define a sequence of instructions providable to the respective fluidic device for operating the respective fluidic device. Thus, the target operation mode may assume ideal conditions, for instance a zero dead volume, and indicates as to how an analysis would be performed when no disturbing real world effects would be present. Or the target operation mode may just indicate performance at a source destination, while the measurement itself relies on the performance at the target destination, for instance at the head of an analytical column.

In contrast to this, the real operation mode may define a realistic behavior of the respective fluidic device upon executing a sequence of instructions by the respective fluidic device for operation. A discrepancy between a device assumed to be ideal and a device in which real world effects are to be considered is manifested in the difference between the real operation mode and the target operation mode. For calculating a real operation mode behavior on the basis of an ideal operation mode, it may be recommendable to model the fluidic device in a specific manner by parameterizing it, and by assigning parameter values so that a specific device may be simulated in a realistic way. Alternatively or in combination, a transfer function can be considered, which represents the behavior of the fluidic device in operation in a condensed mathematical form.

The real operation mode may define a real procedure of treating fluids by the respective fluidic device upon executing the defined sequence of instructions. Therefore, when supplying fluids, for instance constituents of a solvent, to a fluidic device in accordance with a target operation mode at a source destination, the actual outcome in relevant practice at a target destination will be described by the real operation mode.

The first determining unit may be adapted for substituting one of a straight curve section (that is a straight line) and an angled curve section (that is two straight lines aligned along different directions and having one point in common, therefore enclosing an angle) of the first target operation mode by a rounded curve section. Broadening effects or a velocity profile of molecules of a fluidic sample may occur which, for instance, may result from friction between individual components of the fluidic sample and walls of a fluidic conduit. Such effects may, in an actual physical experiment, result in a rounding of curve sections which, in theory or when designing an experiment, are displayed by a number of connected straight curve sections. Thus, rounding a curve in accordance with a physical model of the procedures or effects resulting from one or more laws of nature may be performed when the apparatus displays an actual time dependence of a mixture. This will give a user a realistic impression of the actual conditions within such an apparatus.

More particularly, the first determining unit may be adapted for performing the substitution in accordance with a physical model of a process related to the straight curve section or the angled curve section. Therefore, the physical procedures within the modeled fluidic devices may be taken into account for calculating curves to be visually displayed to a user. In the case when representing the physical behavior by a mathematical transfer function, the first determining unit may be adapted for performing the substitution in accordance with the mathematical translation of a process related to the straight curve section or the angled curve section. Therefore, the transfer function, or a set of transfer functions may be taken into account for calculating curves to be visually displayed to a user.

The first determining unit may be adapted for performing the substitution by calculating a Bezier curve. A Bezier curve may be denoted as a parametric curve (which, generalized to higher dimensions may also be denoted as Bezier surfaces) serving as a tool to model smooth natural curves that can be scaled indefinitely. Such a curve may properly reflect the physical properties within a fluidic device and may allow for performing affine transformations such as translation, scaling and rotation on the Bezier curve.

The first determining unit and/or the second determining unit may be adapted for performing the respective determination by modeling, based on physics, procedures taking place in the respective fluidic devices. Such physical models may be modeled mathematically, for instance in an analytical, numerical and/or phenomenological way and/or empirically extracted transfer functions. Considering such physical procedures may improve the accuracy of the method transfer performed by the apparatus.

The determining unit or units may be adapted for performing the determination by simulating procedures taking place in the fluidic device. Carrying out simulations on the basis of input data parameters may allow to properly consider the parameters influencing the apparatus, thereby allowing to obtain reliable results.

The determining unit or units may be adapted for performing the determination under consideration of laws of nature. For instance, accepted laws of fluid dynamics may be considered by the apparatus.

The apparatus may additionally comprise a third determining unit adapted for determining a second real operation mode of operating the second fluidic device based on the second target operation mode and based on the preknown parameterization of the second fluidic device. After having proposed or suggested a target operation mode for the second fluidic device being the result of the method conversion, it may also be helpful for a user to understand how this target operation mode for the second fluidic device will look like in practice. Thus, in other words, the user may see how the configuration or parameterization of the second fluidic device will affect, in reality, the target curve, for instance how delays will look like and how a rounding of specific curve sections will look like. For more clarity a "difference" trace may be calculated, which allows to quantify matching of the second real operation mode to the first real operation mode.

The first fluidic device may relate to a first product generation, and the second fluidic device may relate to a second product generation succeeding the first product generation. The first product generation may relate to fluidic devices which are brought as products onto the public market before devices according to the second product generation are brought to the market. Thus, the second fluidic device may relate to a further development of the first fluidic device, so that both generations of fluidic devices may basically provide the same functionality, the second fluidic device being only modified with respect to individual items of such a functionality. In such a scenario, it may be appropriate or at least appreciated to use an already practiced or certified method of operating the first fluidic device to, in an amended or modified manner, operate also the second fluidic device.

The apparatus may comprise a user interface adapted for displaying the operation mode visually on a display (such as a liquid crystal display, a cathode ray tube, a plasma display or the like). Such a user interface may include an input unit such as a joystick, a keypad, a button, etc. allowing a user to input commands, data and instruction to the apparatus. Such an output unit may also comprise a data interface allowing a user to connect a peripheral device such as a fluidic device or a memory stick to copy a set of calculated parameters to such an apparatus. With such a user interface, a user may design, store and document a way of operating a fluidic device in a convenient manner.

The user interface may be adapted for displaying the operation mode as graphs. Thus, with a two or three or more dimensional representation, the dependency between different parameters may be plotted in an intuitive manner in a way that the user can get a clear impression of the time dependency of an operation based on what is represented in such a graph. For instance, such a graph may be a two-dimensional coordinate system having an abscissa along which the time is plotted, and may have an ordinate along which a concentration of an individual component of a multicomponent mixture may be plotted.

The system may be adapted as a graphical user interface (GUI) which may be denoted as a user interface which allows people to interact with electronic devices such as computers or handheld devices. Such a GUI may offer graphical icons and visual indicators as opposed to purely text-based interfaces, typed command labels or text navigation to fully represent the information and actions available to a user.

The operation mode or "method" to be proposed by the apparatus may be indicative of a process flow of a separation method such as a chromatographic operation method. Such an operation mode may include a flush procedure, a solvent selection feature, a drive gradient feature (for driving a gradient using a chromatographic column, a further rinse feature, a selected temperature, flow and pressure feature, etc.).

The parameterization or configuration of the fluidic device may include a flow velocity (volume per time), condition of a pump, an inner volume of a pump, a parasitic volume or mixing behavior of fluidic conduits, temperature pressure correlations, delay time, and rise time of a pump, etc.

The device may be adapted for processing a displayed two-dimensional set of data, particularly may be adapted for processing a measurement control curve. Such a measurement control curve may be provided to a measurement apparatus, for instance a chemical analysis unit, a life science apparatus or any other technical apparatus. Adjusting such measurement control data to generate a predefined real operation mode at a target destination may be conventionally a challenge and may be significantly simplified by the intuitive user interface according to an exemplary embodiment.

The multidimensional set of data to be defined may be displayed as a graph. A graph may be denoted as a two- or three-dimensional space which correlates different parameters corresponding to different axes of a coordinate system, for instance two parameters plotted along an abscissa and an ordinate of a two-dimensional Cartesian coordinate system. Such a graph may be continuous, discontinuous, or a set of spaced points. Thus, the graph may be a continuous measurement control curve which can be differentiated at each position. However, also discontinuous graphs which cannot be differentiated at at least one position can be designed according to exemplary embodiments. It is also possible that the graph is simply formed by a number of isolated and spaced points.

The fluidic device may comprise at least one of a sensor device, a test device for testing a device under test or a substance, a device for chemical, biological and/or pharmaceutical analysis, a fluid separation system adapted for separating components of a fluid, an electrophoresis device, a capillary electrophoresis device, a gel electrophoresis device, a capillary electrochromatography device, a liquid chromatography device, a gas chromatography device, an electric measurement device, and a mass spectroscopy device. Thus, exemplary application fields of a fluidic device according to embodiments are gas chromatography, mass spectroscopy, UV spectroscopy, optical spectroscopy, IR spectroscopy, liquid chromatography, and capillary electrophoresis analysis, or bioanalysis. More generally, the device according to embodiments may be integrated in or set aside to an analysis device for chemical, biological and/or pharmaceutical analysis. Such an analysis system may be a fluid separation device, a gas or liquid chromatography device, an electrophoresis system, a capillary electrochromatography system, or the like. In a realization of the apparatus as a device for chemical, biological and/or pharmaceutical analysis, functions like (protein) purification, electrophoresis investigation, fluid separation, or chromatography investigations may be realized by the analysis device. An example for a fluidic device is an apparatus of the 1100 Series for liquid chromatography (LC) of Agilent Technologies.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

Figure 1:
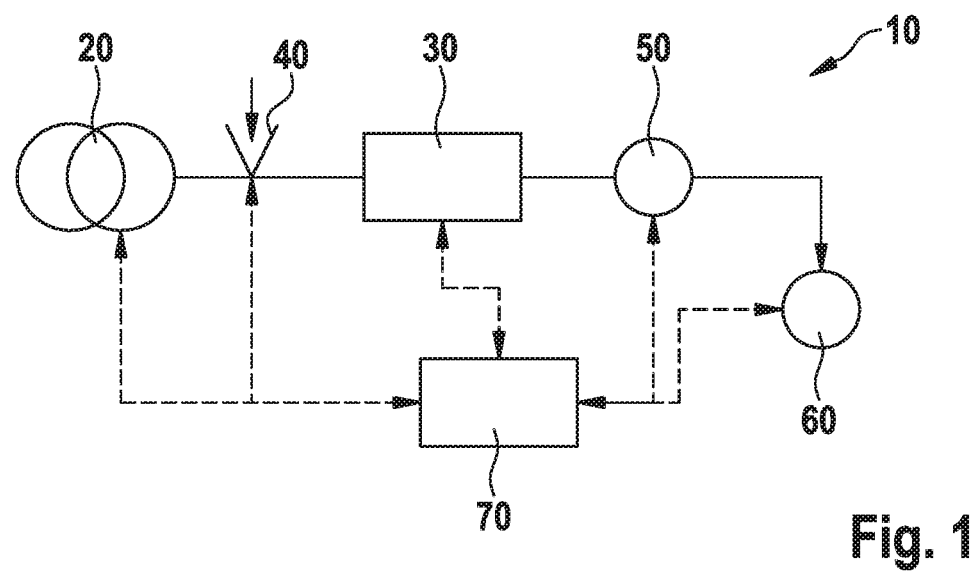
FIG. 1 shows a liquid separation system, in accordance with embodiments of the present invention, e.g. used in high performance liquid chromatography (HPLC).

The illustrations in the drawings are schematic.

Referring now in greater detail to the drawings, FIG. 1 depicts a general schematic of a liquid separation system 10. A pump 20—as a mobile phase drive—drives a mobile phase through a separating device 30 (such as a chromatographic column) comprising a stationary phase. A sampling unit 40 can be provided between the pump 20 and the separating device 30 for introducing a sample fluid to the mobile phase. The stationary phase of the separating device 30 is adapted for separating compounds of the sample liquid. A detector 50 is provided for detecting separated compounds of the sample fluid. A fractionating unit 60 can be provided for outputting separated compounds of sample fluid.

A data processing unit 70, which can be a PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the sampling unit (e.g. controlling an amount for sampling, controlling sample injection or synchronizing sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70, and send information (e.g. about the detected sample compounds) to the data processing unit 70. The data processing unit 70 might also control operation of the fractionating unit 60 (e.g. in conjunction with data received from the detector 50) and provide data back.

In the following, referring to FIG. 2, an apparatus 200 (which may be the data processing unit 70 or which may provide control commands to the data processing unit 70) for converting an operation mode such as a liquid chromatography method of an possibly already certified fluidic device (not shown) for the fluidic device 10 according to an exemplary embodiment will be explained.

In this representation, the fluidic device 10 modeled with or controlled by the apparatus 200 is capable of mixing multiple components of a solvent at a source position of the fluidic device 10 at which individual components of the solvent are supplied, for instance from vials (not shown). The fluidic device 10 will, supported by one or more pumps 20, transport the mixture of the solvent constituents to a destination position such as an inlet of the chromatographic column 30. This procedure may represent at least part of the LC method to be converted for the fluidic device 10.

The apparatus 200 comprises an input/output unit 208 via which a user may input data 210 into the system. The input data 210 may include instructions for controlling performance of the apparatus 200 and may additionally or alternatively also include data parameters used for an analysis or design of a performance of the already certified fluidic device. More particularly, such an already certified or first fluidic device is characterized by a first target operation mode representing a desired behavior of the first fluidic device and by a first real operation mode representing the actual behavior of the first fluidic device during a practical LC analysis. In a similar manner, also in the second fluidic device 10, there may be a discrepancy between a second target operation mode representing a desired behavior of the second fluidic device 10 and a second real operation mode representing the actual behavior of the second fluidic device 10.

The input data 210 provided to a first determining unit 202 of the apparatus 200 is indicative of the first target operation mode and a preknown parameterization (or configuration) of the first fluidic device. On the basis of this data, the first determining unit 202 may determine the first real operation mode of the first fluidic device.

Figure 3:
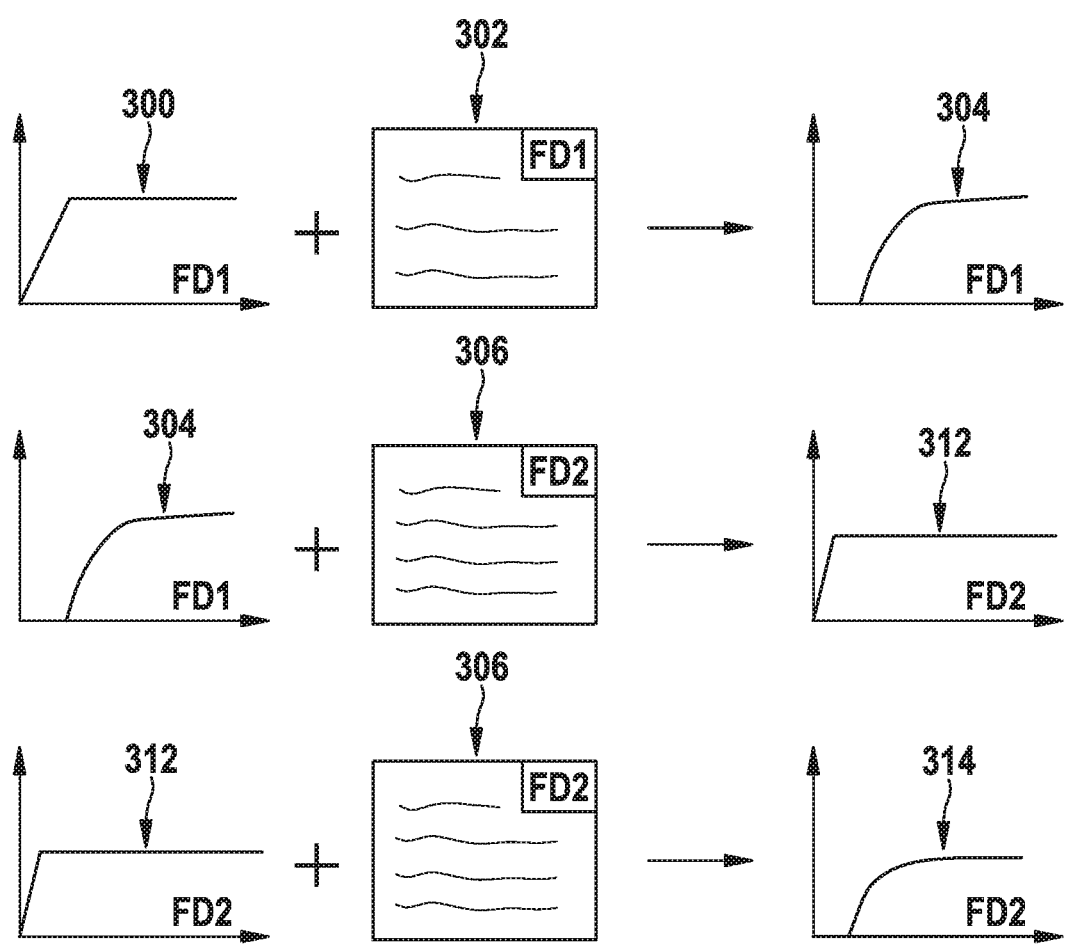
FIG. 3 schematically illustrates a method of converting an operation mode from a first fluidic device to a second fluidic device according to an exemplary embodiment.

FIG. 3 illustrates the procedures connected with this determination. Reference numeral 300 denotes a first target operation mode of the first fluidic device. Since this is an ideal operation mode, the shown characteristic is a linear increase of a concentration of a solvent component over time, followed by a time interval during which this concentration is constant. This piece of information in combination with the preknown parameterization 302 of the first fluidic device, i.e. a data set indicating the physical properties of the fluidic device may allow the first determining unit 202 to derive the first real operation mode 304. The discrepancy between the curves 300 and 304 results from the fact that delays result due to the physical extension of the flow path of the fluid, i.e. due to the dwell volume of the fluidic device. In addition to this, broadening effects resulting from velocity and temperature profiles across fluidic conduit lead to a rounding of the angled curve 300. Thus, modeling the technical system represented by the first fluidic device in combination with the target operation mode 300 allows the first determining unit 202 to derive the first real operation mode 304.

Figure 2:
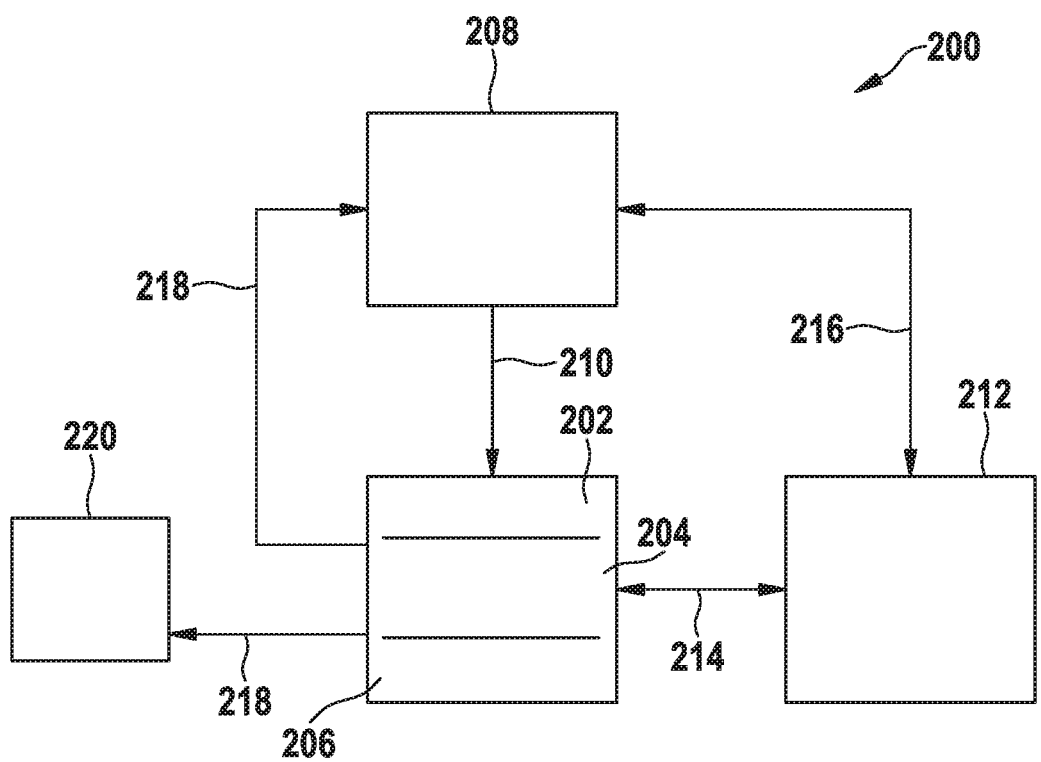
FIG. 2 shows a system for converting an operation mode from a first fluidic device to a second fluidic device according to an exemplary embodiment.

Coming back to FIG. 2, the apparatus 200 further comprises a second determining unit 204 adapted for determining a second target operation mode 312 of the second fluidic device based on the determined first real operation mode 304 of the first fluidic device and based on a preknown parameterization of the second fluidic device 306. Hence, optionally under consideration of the first target operation mode 300 and/or the first preknown parameterization 302, it is possible to calculate or at least approximate the second target operation mode 312 of the second fluidic device. In view of the knowledge of the real characteristics of the operation mode due to the preknown configuration of the first fluidic device, similar discrepancies between the target and the real operation mode of the second fluidic device may occur. Thus, by taking reasonable assumptions, performing a numerical analysis, preparing a physical model of the fluidic devices, including an iterative approach, using elements of artificial intelligence (such as neural networks and/or Fuzzy logic), etc., it is possible for the system to calculate or at least estimate the second target operation mode 312 of the second fluidic device on the basis of the mentioned data and assumptions. This allows for a method transfer from the first fluidic device to the second fluidic device.

A third determining unit 206 of the apparatus 200 is adapted for determining a second real operation mode 314 of the second fluidic device based on the second target operation mode 312 and based on the preknown parameterization of the second fluidic device 306. This task can be performed in a similar manner as the calculation of the first real operation mode 304 on the basis of the first target operation mode 300 and the first preknown configuration 302 of the first fluidic device.

For performing these calculations, the determining units 202, 204, 206 (which may be realized as a common processor or as separate processors) may use a preknown parameterization or configuration of the fluidic devices. This data can be obtained from a database 212 (such as a memory, for instance a hard disk) which is in bidirectional data exchange communication 214 with the determining units 202, 204, 206. The database 212 may store data indicative of an operation or technical specification of the fluidic devices. The database 212 may also be in bidirectional data communication 216 with the input/output unit 208 to allow a user to download data from the database 212 or to allow the user, via the input/output unit 208, to store data regarding a measurement device in that database 212.

Output data 218 indicative of the derived second target operation mode 312 of the second fluidic device (and, if desired, additional data) may be supplied to the input/output unit 208 for visual display, etc.

As can further be taken from FIG. 2, additionally or alternatively to the provision of the data 218 to the input/output unit 208, the determination units 202, 204, 206 may also supply this data 218 as control data to a connected fluidic device 220 for correspondingly driving this fluidic device. This may be one of the first and the second fluidic devices. Thus, when the determination units 202, 204, 206 have determined the parameters required for an operation of the fluidic device 220 in such a manner that the desired method defined by the user is carried out, this data 218 can be directly used as control parameters for correspondingly operating the fluidic device 220.

Figure 4:
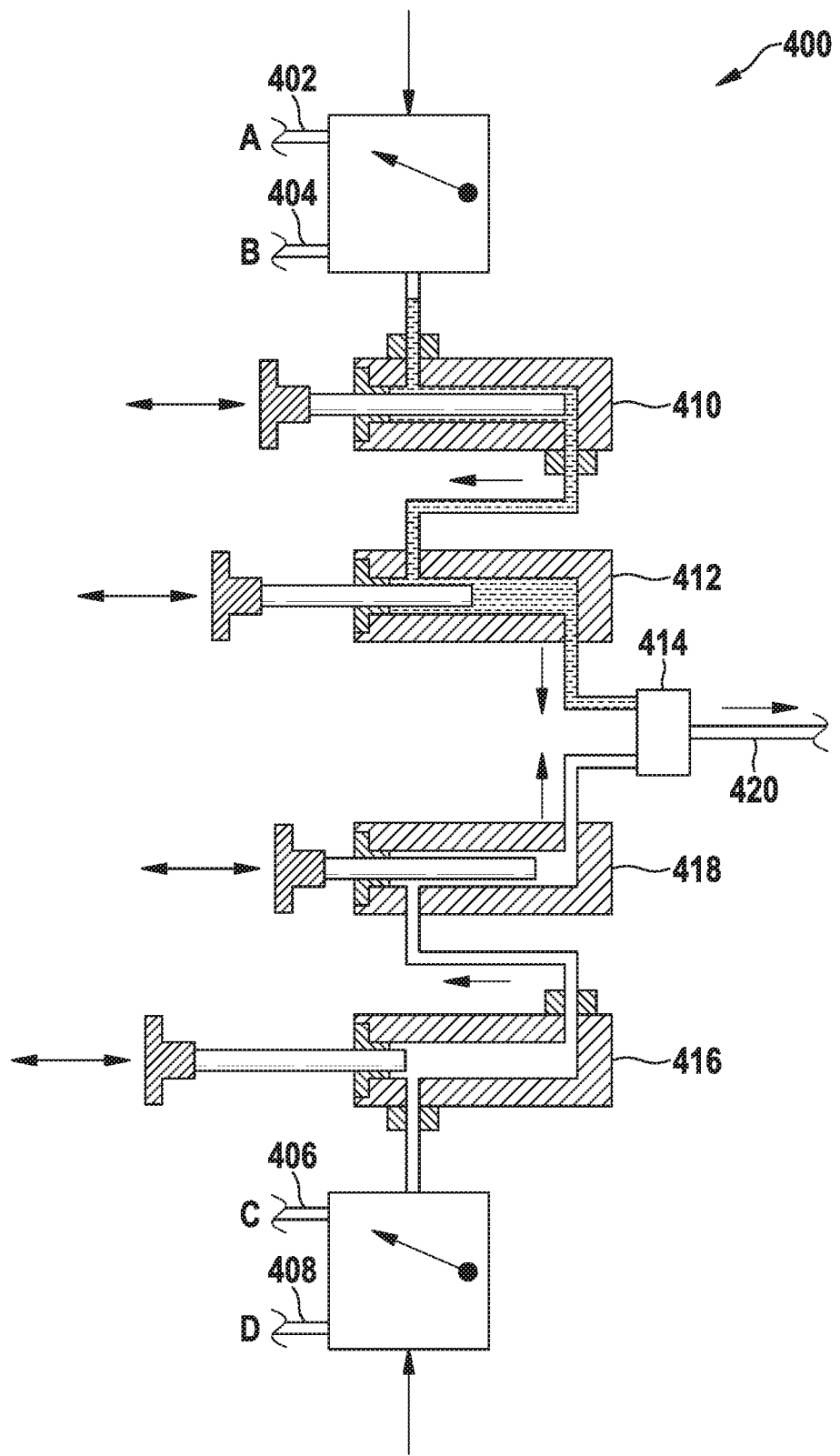
FIG. 4 illustrates a pump configuration with a quaternary pump of a fluidic device considered according to an exemplary embodiment.

FIG. 4 illustrates a pump system 400 of a fluidic device.

At a first source position 402, a first component A of a solvent is supplied. At a second source position 404, a second component B is supplied. At a third source position 406, a third component C for the solvent is supplied. At a fourth source position 408, a fourth component D is provided. The components A and B are supplied to a first pump 410 and subsequently to a second pump 412 before being provided to a mixing unit or T-piece 414. The components supplied at source positions 406 and 408 are pumped by a third pump 416 and by a fourth pump 418 before being supplied to the mixing unit 414. An output of the mixing unit 420 including a mixture of at least a part of components A, B, C, and D may be denoted as a destination position at which the system 400 is connected to a liquid chromatography separation column (not shown, but constituted in a similar manner as reference numeral 30 in FIG. 1) for subsequent LC analysis, for instance defining a gradient on the column 30.

For the determination performed by the determination units 202, 204, 206, the system 400 is modeled in the apparatus 200 and the user can read for instance at the input/output unit 208 which time dependency of the concentration is desired at the destination position 420, i.e. which solvent constitution should be supplied to the chromatographic column 30. The system will then perform a calculation considering the performance of the pumps 410, 412, 416, 418 as well as internal volumes of the various conduits in FIG. 4, temperature and velocity profiles within the conduits of the system 400, or the like so as to calculate the data indicating how (particularly when and in which amount) the different substances 402, 404, 406, 408 are to be supplied. This input/output unit 208 may also display traces for the user to allow to distinguish between a desired target time dependency at a source destination (inlet of 410) and a real time dependency at a target destination like 420.

Thus, the complex pump configuration 400, which can also be any hybrid system including any desired n-ternary pump configuration (for instance a stack of two quaternary pumps) may be taken into account to set up an appropriate gradient for the chromatographic column 30, and to transfer a corresponding method from one LC device to another one.

Figure 5:
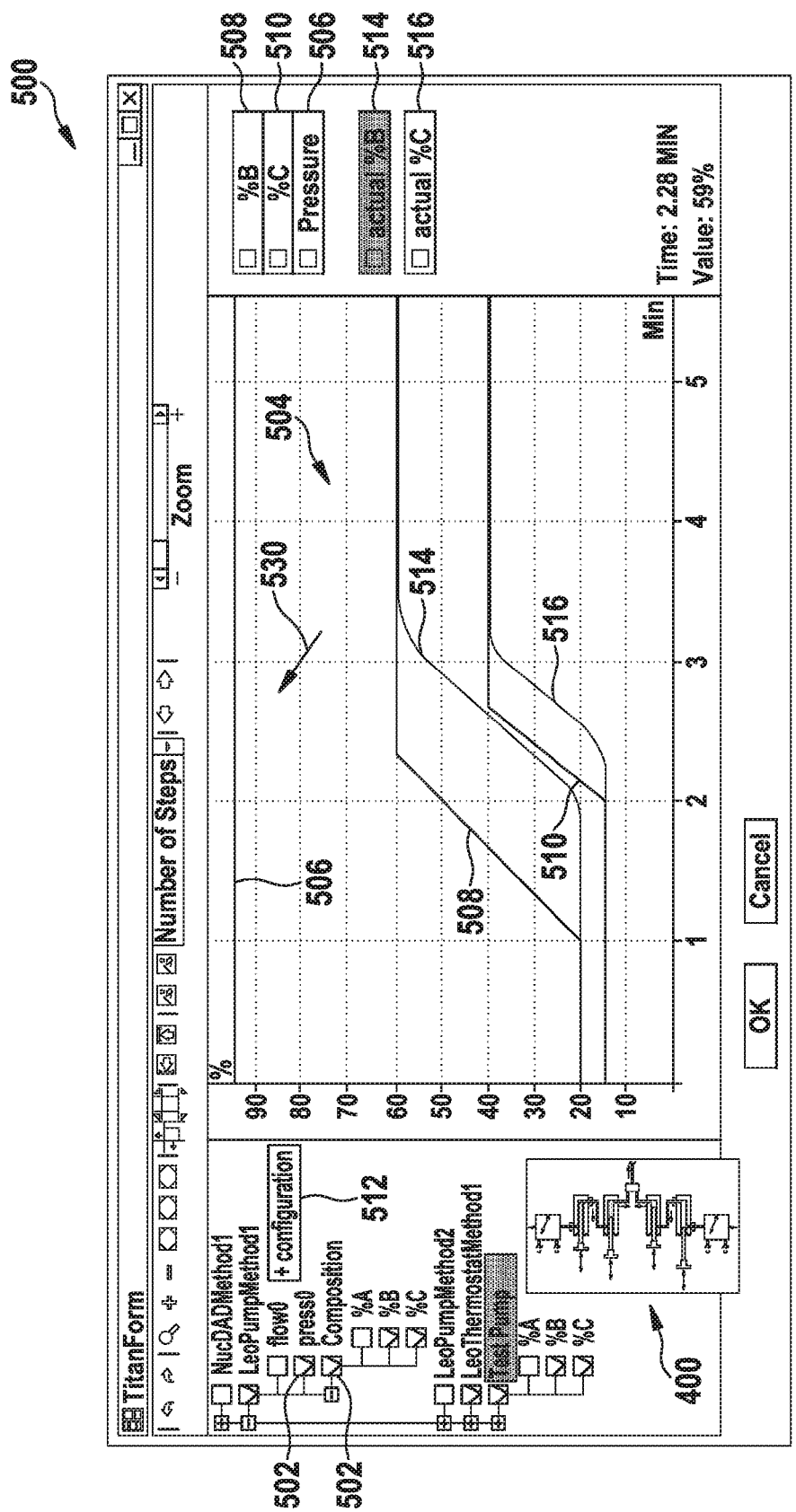
FIG. 5 illustrates a graphical user interface enabling a user for adjusting an operation mode of a liquid chromatography device according to an exemplary embodiment.

FIG. 5 shows a graphical user interface 500 according to an exemplary embodiment via which a user may monitor (and define in an interactive manner) a desired time sequence as to how the different components A, B, C, D are to be provided at the destination position 420 in accordance with a target method. The graphical user interface 500 also displays curves showing how the configuration (described by a corresponding parameterization) of the corresponding LC device will influence the actually obtained result in a practical experiment.

The user interface 500 comprises a number of check fields 502 (each of which being activatable or deactivatable by for instance a mouse click) via which a number of parameters can be adjusted for the simulation displayed in a diagram 504. For instance, it can be adjusted which constituents of the solvent A, B, C, D should be taken into account for a specific application. In the diagram 504, a number of graphs are then plotted showing desired values of the corresponding solvent concentrations and corresponding actual values which can be obtained when considering realistic effects within the device 400.

For instance, the diagram 504 shows a pressure curve 506 indicative of the pressure conditions within the system 400. Furthermore, for the present scenario of FIG. 5 that only components B and C are mixed with A, a first ideal concentration curve 508 regarding component B is plotted. Moreover, a second ideal concentration curve 510 regarding component C is plotted. The ideal curves 508, 510 are angled and are indicative of a linear increase of the corresponding partial concentrations between time intervals during which the corresponding partial concentrations remain constant. Considering a configuration 512 of the system 400, i.e. the technical parameters of the physical device 400 stored in the database 212, an actual or real curve 514 of the concentration of constituent B is obtained which corresponds to the ideal curve 508. In a similar manner, the actual conditions of the concentration profile of component C are plotted as a curve 516 which corresponds to the ideal curve 510.

For instance, when the time dependence of supplying the component B is adjusted for the device 400 in accordance with curve 508, at the destination of the device 400 the curve 514 is obtained. When the concentration of the component C is adjusted in accordance with curve 510 at the corresponding source, the profile 516 is obtained at the destination. Thus, with the user interface 500, a user can see as to how the pump configuration 400 has an effect on the actual constituent of the components B and C. Then, using a mouse pointer 530 operated by a computer mouse or the like, the user may manipulate the individual curves in the diagram 504 until a desired actual sequence is obtained.

According to an exemplary embodiment, the various curves 300, 304, 312, 314 may be displayed and/or manipulated by the user. Also the parameterization of the corresponding fluidic devices may be input and/or displayed via the user interface 500.

Figure 6:
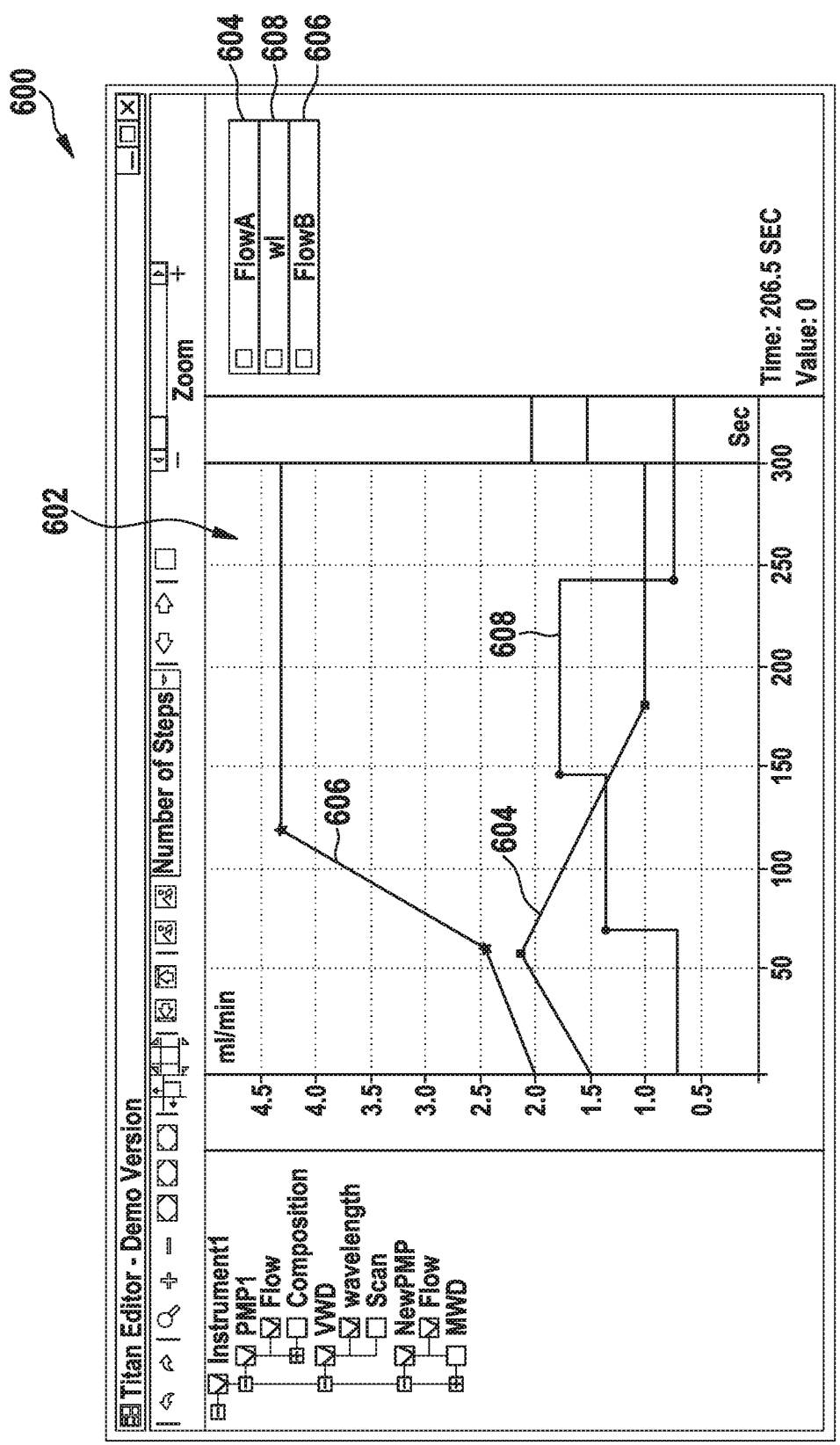
FIG. 6 and FIG. 7 show screenshots of a graphical user interface allowing to manipulate a graph.
Figure 7:
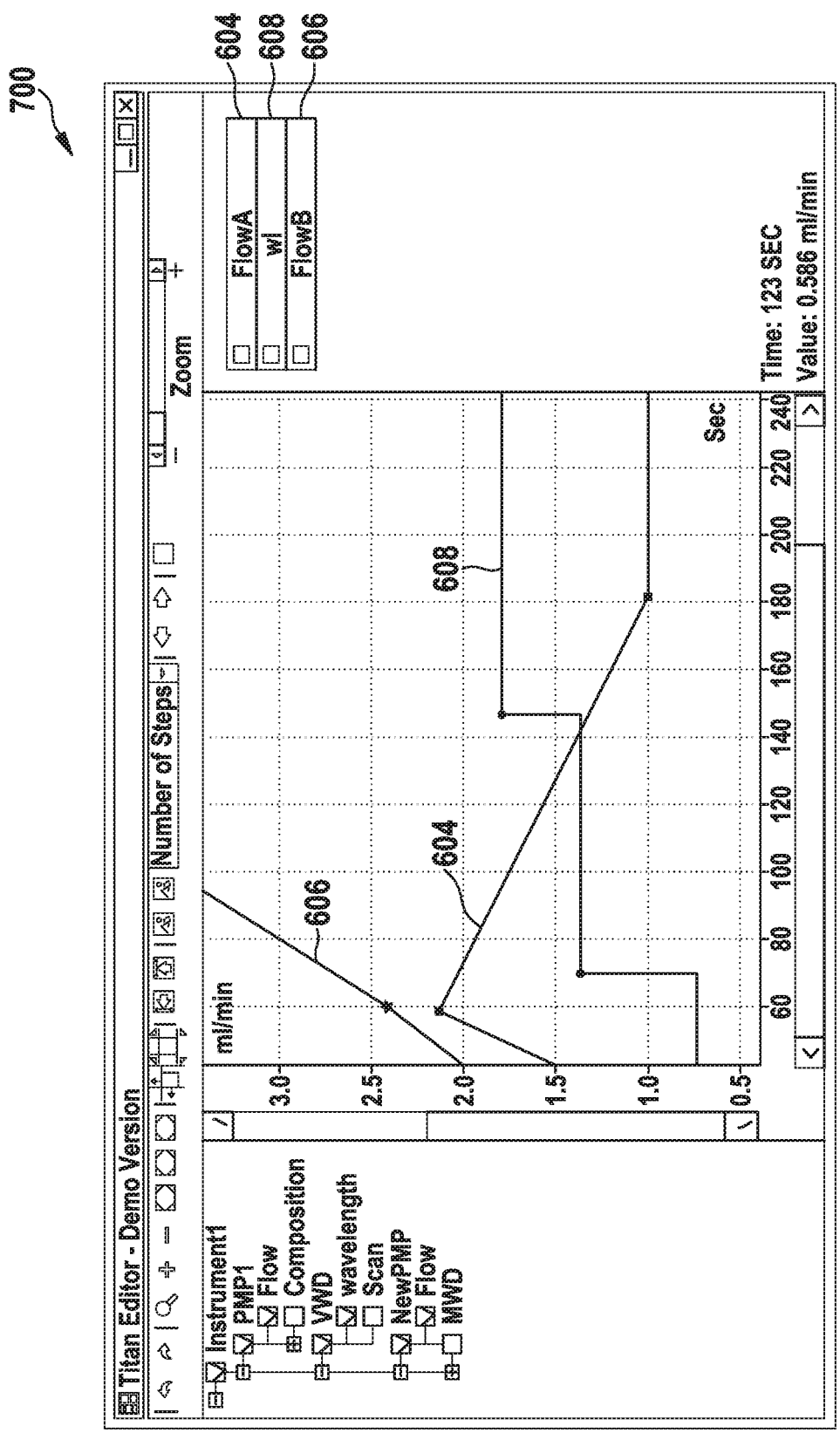

FIG. 6 shows a screenshot 600 of a user interface according to an exemplary embodiment illustrating a diagram 602 including a flow of a first component A 604, a flow of a second component B 606 and a third control parameter 608. As can be taken from a comparison with a screenshot 700 shown in FIG. 7, the user interface provides the opportunity to overlay graphs from every module to view or edit them at once. Furthermore, zoom and scroll functions are provided for viewing at a higher resolution.

Figure 8:
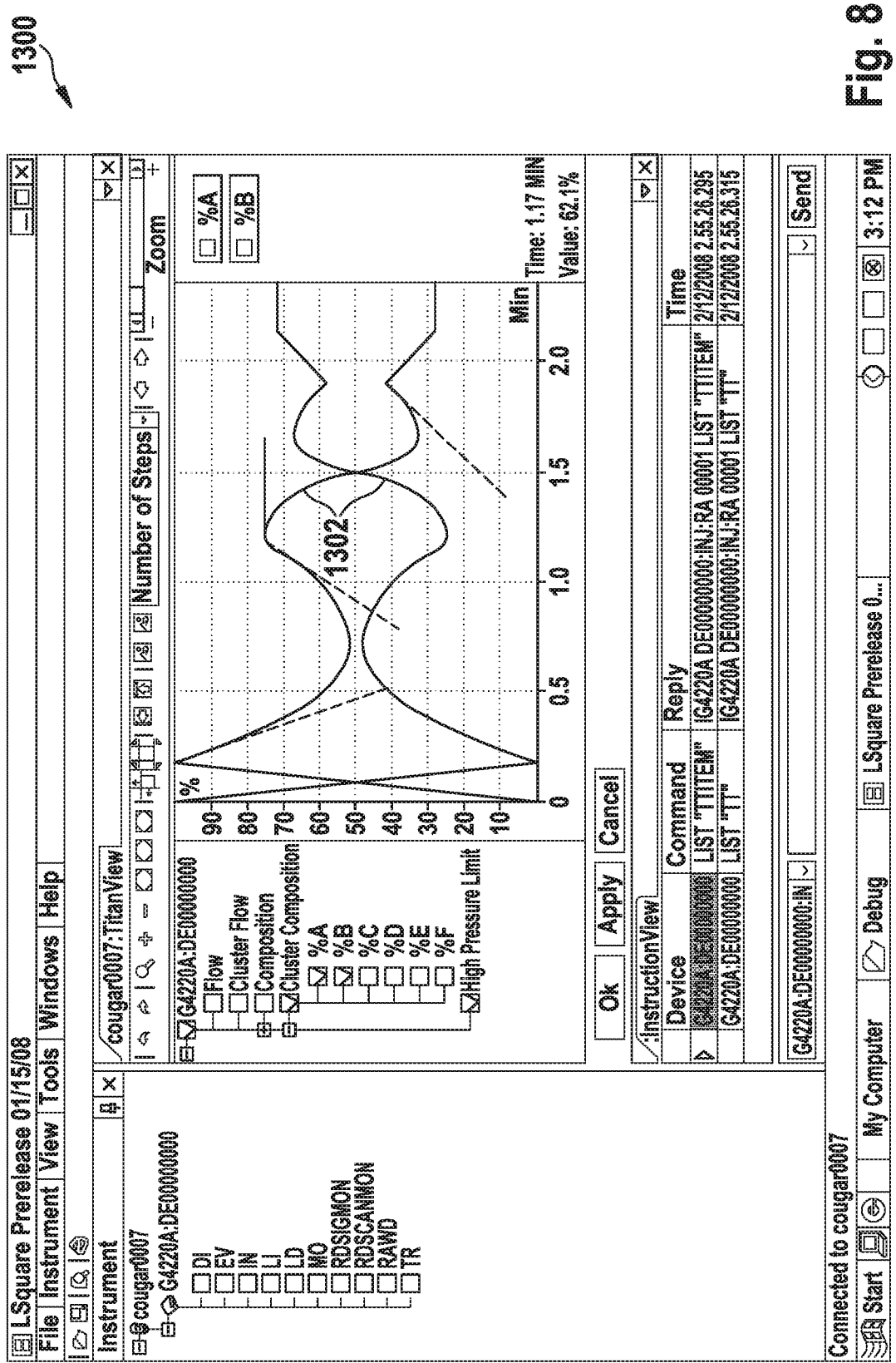
FIG. 8 illustrates a user interface according to an exemplary embodiment displaying Bezier curves for programming an operation mode according to physical effects.

A screenshot 1300 shown in FIG. 8 shows a number of Bezier curves 1302 being a simple but precise way to display and allow modifications to free style program changes. The setting up is intuitive. Resulting controls can be squeezed into tables. Execution is easy to implement. FIG. 8 shows a graph of the percentage of a composition programmed with Bezier curves 1302.

Figure 9:
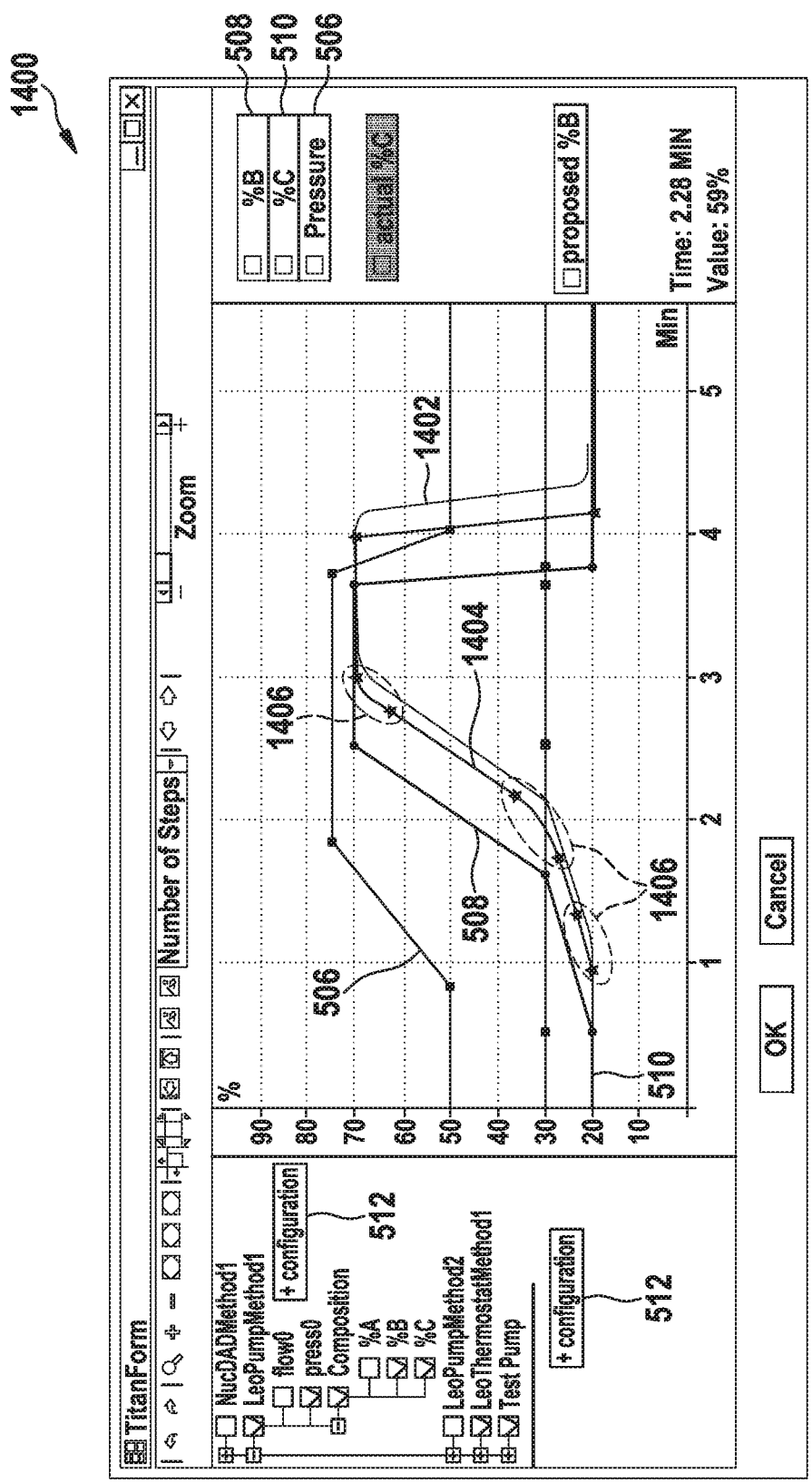
FIG. 9 illustrates a graphical user interface which can be used for performing a method transfer.

FIG. 9 shows a further screenshot 1400 indicating how a method transfer functionality is a use case for Bezier curves.

Considering the configurations 512 of the system 400 in a first and in a second implementation, an actual value 1402 for the concentration of component B is calculated, considering a first target operation mode 508 of the first configuration of a fluidic device at a source destination. This actual value 1402 represents the real operation mode at the target destination. Furthermore, a specific concentration for component B may be proposed, as a second operation mode, see curve 1404. The second operation mode 1404 being derived from the actual value 1402, while considering the second configuration 512 of the system 400 in its second implementation. Basically the curve 1404 represents the operation mode required for system 400 in second configuration to exhibit the same performance at the target destination as system 400 in first configuration did in response to first operation mode 508. To control such a curve 1404 more precisely, curve sections 1406 may be programmed as Bezier curves rather than purely straight or angled sections.

Different methods exist which can be implemented according to exemplary embodiments to model delay volume (or dwell volume, gradient volume, transition volume) which is presently considered as one of the main origins of a discrepancy between a target value and an actually achieved value of a concentration provided by a pump device such as a pump system 400.

The dwell volume may be denoted as the system volume from the point of the mobile phase mixing to the column head. Different dwell volumes may result in a time shift (i.e. the time for the mobile phase to reach the column head). Additionally, the dwell volume may affect the gradient shape (dispersion effects, flush out behavior, etc.). Thus, the programmed gradient may become deteriorated. Even with a same delay volume, the chromatographs can look different on different systems when the flush out behavior is different. The dwell volume may have a significant impact especially for narrow bore applications, especially combined with fast gradient.

According to one embodiment, dwell volume determination may be done in a way as disclosed by John W. Dolan, "Dwell Volume Revisited", LCGC North America. Volume 24, No. 5, May 2006, pages 458 to 466. In accordance with this, it is possible to measure the dwell time by drawing a tangent to a main part of the gradient curve and extend the baseline to intersect this tangent. The time it takes from the start of the program to this intersection may be denoted as the dwell time. This may be multiplied with the flow rate to get the dwell volume. The corresponding disclosure of Dolan 2006 is incorporated by reference.

According to another exemplary embodiment, calculation of the dwell volume may be performed on a step of a gradient, not on a linear gradient. With such an embodiment, the delay volume is close to the physical volume (when the gradient starts to hit the column) Transition volumes reflect the dispersion effects (i.e. how much a program gradient becomes deteriorated). Such a dwell volume calculation which may be implemented according to an exemplary embodiment, is disclosed by G. Hendriks et al. "New practical algorithm for modeling retention times in gradient reversed-phase high-performance liquid chromatography", Journal of Chromatography A, 1089 (2005), pages 193 to 202. The corresponding disclosure of Hendriks 2005 is incorporated by reference.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. An apparatus that converts an operation for controlling a first fluidic device to a corresponding operation for controlling a second fluidic device, the apparatus comprising:
   an input/output device programmed to receive a first target operation for treating a first fluid by the first fluidic device, wherein the first target operation defines a sequence of instructions for controlling the first fluidic device;
   a database configured to store modeling parameters for the first and second fluidic devices; and
   a processor programmed to:
   receive the first target operation from the input/output device and receive the modeling parameters for the first and second fluidic devices from the database,
   determine a real operation based on the first target operation and the modeling parameters of the first fluidic device, wherein the real operation represents actual behavior of treating the first fluid when controlling the first fluidic device with the first target operation,
   determine a second target operation, for treating a second fluid by the second fluidic device, based upon the real operation and the modeling parameters of the second fluidic device, wherein the second target operation defines a sequence of instructions for controlling the second fluidic device; and
   control the operation of the second fluidic device for treating the second fluid according to the determined second target operation, or transfer the determined second target operation to a data processing unit for controlling the operation of the second fluidic device for treating the second fluid according to the determined second target operation.

2. The apparatus of claim 1, wherein the first target operation defines at least one of the group consisting of:
   analyzing a medication,
   analyzing a biological sample,
   mixing various fluids,
   performing diagnostics,
   requiring official approval,
   requiring official certification,
   flushing the respective fluidic device,
   selecting a solvent,
   applying a concentration gradient, and
   selecting an operation temperature.

3. The apparatus of claim 1, wherein the modeling parameters of the first and second fluidic devices define physical properties of the respective first or second fluidic devices.

4. The apparatus of claim 3, wherein the modeling parameters of each of the first and second fluidic devices define a physical property of a size of the respective first and second fluidic device, a volume of a fluid conduit of the respective first and second fluidic device, a pump performance of the respective first and second fluidic device, a delay parameter of operating the respective first and second fluidic device, a friction parameter indicative of friction occurring when operating the respective first and second fluidic device, a flush performance of the respective first and second fluidic device, and a combination or cooperation of different components of the respective first and second fluidic device.

5. The apparatus of claim 1, wherein for determining the real operation, the processor is programmed to replace one of a straight curve section and an angled curve section of the first target operation with a rounded curve section.

6. The apparatus of claim 5, wherein the processor is programmed to perform at least one of:
the substitution in accordance with a physical model of a process relating to the straight curve section or the angled curve section; and
the substitution by calculating a Bezier curve.

7. The apparatus of claim 1, wherein the processor is programmed to perform at least one of:
modeling, based on physics, procedures taking place in the respective first and second fluidic devices, and/or based on a transfer function extracted empirically; and
simulating physical properties or procedures taking place in the respective first and second fluidic devices.

8. The apparatus of claim 1, wherein the processor is further programmed to generate another real operation based upon the second target operation and the modeling parameters of the second fluidic device, wherein the other real operation represents actual behavior of treating the second fluid when controlling the second fluidic device with the second target operation.

9. The apparatus of claim 8, wherein: the processor is further programmed to determine a difference between the real operation and the other real operation; and the input/output device is programmed to display the determined difference for qualifying the performance of operating the second fluidic device.

10. The apparatus of claim 1, wherein the input/output device is further programmed to display at least a part of one or more of the first target operation, second target operation, and real operation on a display device.

11. The apparatus of claim 10, wherein the input/output device is further programmed to perform at least one of: displaying the at least part of the first target operation, second target operation, or real operation as a graph; enabling a user to manipulate at least one of the first target operation, second target operation, and real operation; and updating at least another one of the first target operation, second target operation, and real operation upon manipulation of the at least one of the first target operation, second target operation, and real operation by the user.

12. The apparatus of claim 1, wherein: the first fluidic device and the second fluidic device are one of the group consisting of fluid separation devices configured for separating compounds of a fluid, fluid purification devices, measurement devices, life science devices, sensor devices, devices for chemical, biological and/or pharmaceutical analysis, capillary electrophoresis devices, liquid chromatography devices, capillary electrochromatography devices, HPLC devices, gas chromatography devices and mass spectroscopy devices; the first fluidic device relates to a first product generation and the second fluidic device relates to a second product generation succeeding the first product generation; the first target operation, second target operation, and real operation are chromatographic methods; or the input/output device is programmed to display at least a part of one or more of the first target operation, second target operation, and real operation on a display device.

13. An apparatus that converts an operation for controlling a first fluidic device to a corresponding operation for controlling a second fluidic device, the apparatus comprising:
an input/output device programmed to receive a first target operation for treating a first fluid by the first fluidic device, wherein the first target operation defines a sequence of instructions for controlling the first fluidic device;
a database configured to store transfer functions representing the physical behaviors of the first and second fluidic devices; and
a processor programmed to:
receive the first target operation from the input/output device and receive the transfer functions for the first and second fluidic devices from the database,
determine a second target operation, for treating a second fluid by the second fluidic device, based upon the real operation and the modeling parameters of the second fluidic device, wherein the second target operation defines a sequence of instructions for controlling the second fluidic device; and
control the operation of the second fluidic device for treating the second fluid according to the determined second target operation, or transfer the determined second target operation to a data processing unit for controlling the operation of the second fluidic device for treating the second fluid according to the determined second target operation.

14. The apparatus of claim 13, wherein the processor is further programmed to generate a real operation based upon the second target operation and the transfer function of the second fluidic device, wherein the real operation represents actual behavior of treating the second fluid when controlling the second fluidic device with the second target operation.

15. The apparatus of claim 14, wherein: the processor is further programmed to: generate another real operation based upon the first target operation and the transfer function of the first fluidic device, wherein the other real operation represents actual behavior of treating the first fluid when controlling the first fluidic device with the first target operation, and determine a difference between the other real operation and the real operation; and the input/output device is programmed to display the determined difference for qualifying the performance of operating the second fluidic device.

16. The apparatus of claim 13, wherein the transfer functions of the first and second fluidic devices define physical properties of the respective first or second fluidic devices.

17. The apparatus of claim 13, wherein the input/output device is further programmed to display at least a part of one or more of the first target operation, second target operation, and real operation on a display device.

18. A method, executed by a processor, for converting an operation for controlling a first fluidic device to a corresponding operation for controlling a second fluidic device, the method comprising:

receiving, through an input/output device, a first target operation for treating a first fluid by the first fluidic device, wherein the first target operation defines a sequence of instructions for controlling the first fluidic device;

receiving, from a database, modeling parameters for the first and second fluidic devices;

determining a real operation based on the first target operation and the modeling parameters of the first fluidic device, wherein the real operation represents actual behavior of treating the first fluid when controlling the first fluidic device with the first target operation;

determining a second target operation, for treating a second fluid by the second fluidic device, based upon the real operation and the modeling parameters of the second fluidic device, wherein the second target operation defines a sequence of instructions for controlling the second fluidic device; and controlling the operation of the second fluidic device for treating the second fluid according to the determined second target operation, or transferring the determined second target operation to a data processing unit for controlling the operation of the second fluidic device for treating the second fluid according to the determined second target operation.

19. The method of claim 18, further comprising:

generating another real operation based upon the second target operation and the modeling parameters of the second fluidic device, wherein the other real operation represents actual behavior of treating the second fluid when controlling the second fluidic device with the second target operation.

20. A computer program or product, comprising instructions stored on a non-transitory computer readable medium, for controlling or executing the method of claim 18, when run on a data processing system.

21. A liquid chromatograph comprising:

a liquid chromatograph unit which includes an elution unit sending an eluent to a detecting unit; and a control unit programmed to control elution performed by the elution unit based on a predetermined time table, wherein the control unit includes:

a storage unit configured to store an elution response of the liquid chromatograph unit to be obtained when a predetermined command value is input to the elution unit and an elution response of another liquid chromatograph to be obtained when the command value is input to another elution unit of another liquid chromatograph, a first processing unit programmed to convert the time table based on an elution profile and another elution response such that the elution response at the time when the elution unit is controlled by the liquid chromatograph unit based on the time table approaches another elution profile at the time when another elution unit is controlled by another liquid chromatograph based on the time table, and a second processing unit programmed to divide the converted time table into a plurality of regions, and the second processing unit performs approximate calculation for each of the divided regions and supplies a signal to the elution unit based on the result of the approximate calculation.

22. The liquid chromatograph according to claim 21, wherein the second processing unit programmed to perform polynomial approximation as the approximate calculation.

23. The liquid chromatograph according to claim 21, wherein the second processing unit is programmed to changes the region into which the time table is divided based on whether an approximation error exceeds a predetermined threshold value as a result of the approximate calculation.

24. The liquid chromatograph according to claim 21, wherein the second processing unit is programmed to changes the region into which the time table is divided to be larger in a case where an approximation error does not exceed a predetermined threshold value as a result of the approximate calculation.

25. The liquid chromatograph according to claim 24, wherein the second processing unit is programmed to sets an upper limit in advance at the size of the region to be divided.

26. A method of processing data of a liquid chromatograph, the method comprising:

a process of acquiring a first elution response regarding a first liquid chromatograph by detecting an elution profile when a predetermined command value is input to an elution unit of the first liquid chromatograph;

a process of acquiring a second elution response regarding a second liquid chromatograph by detecting an elution profile when the command value is input to an elution unit of the second liquid chromatograph;

a process of converting a time table based on the first elution response and the second elution response such that a first elution profile at the time when the elution unit is controlled by the first liquid chromatograph based on a predetermined time table approaches a second elution profile at the time when the elution unit of the second liquid chromatograph is controlled by the second liquid chromatograph based on the time table;

a process of dividing the converted time table into a plurality of regions;

a process of performing approximate calculation for each of the divided regions; and a process of supplying a signal to the elution unit of the first liquid chromatograph based on the results of the approximate calculation.

* * * * *